United States Patent
Kauffman et al.

(10) Patent No.: US 11,667,816 B2
(45) Date of Patent: Jun. 6, 2023

(54) HOT MELT ADHESIVE COMPOSITIONS INCLUDING NON-SINGLE SHE CATALYZED AMORPHOUS POLY ALPHA-OLEFIN POLYMER, AND ARTICLES INCLUDING THE SAME

(71) Applicant: H.B. Fuller Company, St. Paul, MN (US)

(72) Inventors: Thomas F. Kauffman, Woodbury, MN (US); Steven R. Vaughan, Lake Elmo, MN (US); Yiming Zeng, Minneapolis, MN (US)

(73) Assignee: H.B. Fuller Company, St. Paul, MN (US)

( * ) Notice: Subject to any disclaimer, the term of this patent is extended or adjusted under 35 U.S.C. 154(b) by 712 days.

(21) Appl. No.: 16/685,733

(22) Filed: Nov. 15, 2019

(65) Prior Publication Data
US 2020/0157385 A1    May 21, 2020

Related U.S. Application Data

(60) Provisional application No. 62/885,568, filed on Aug. 12, 2019, provisional application No. 62/767,793, filed on Nov. 15, 2018.

(51) Int. Cl.
| | | |
|---|---|---|
| *C09J 7/35* | (2018.01) | |
| *C09J 7/29* | (2018.01) | |
| *B32B 5/02* | (2006.01) | |
| *B32B 7/12* | (2006.01) | |
| *B32B 27/12* | (2006.01) | |
| *C09J 11/08* | (2006.01) | |

(52) U.S. Cl.
CPC .............. *C09J 7/35* (2018.01); *B32B 5/022* (2013.01); *B32B 7/12* (2013.01); *B32B 27/12* (2013.01); *C09J 7/29* (2018.01); *C09J 11/08* (2013.01); *B32B 2555/02* (2013.01); *C09J 2400/263* (2013.01); *C09J 2423/00* (2013.01); *C09J 2423/10* (2013.01); *C09J 2491/00* (2013.01)

(58) Field of Classification Search
USPC .................................................. 524/505, 528
See application file for complete search history.

(56) References Cited

U.S. PATENT DOCUMENTS

| | | | |
|---|---|---|---|
| 3,362,940 A | | 1/1968 | Edwards et al. |
| 4,826,909 A † | | 5/1989 | Lakshmanan |
| 4,956,207 A † | | 9/1990 | Kauffman |
| 5,723,546 A | | 3/1998 | Sustic |
| 5,763,333 A | | 6/1998 | Suzuki et al. |
| 6,218,457 B1 | | 4/2001 | Fralich et al. |
| 6,582,829 B1 * | | 6/2003 | Quinn ................ C09J 123/0815 524/505 |
| 7,262,251 B2 | | 8/2007 | Kanderski et al. |
| 8,487,026 B2 | | 7/2013 | Bach et al. |
| 9,670,388 B2 | | 6/2017 | Bunnelle |
| 9,695,340 B2 | | 7/2017 | Moriguchi et al. |
| 9,783,712 B2 | | 10/2017 | Hamann et al. |
| 2014/0079919 A1 | | 3/2014 | Bunnelle |
| 2015/0037579 A1 * | | 2/2015 | Juers ...................... C08L 53/02 524/570 |
| 2015/0174286 A1 † | | 6/2015 | Bunnelle |
| 2017/0029670 A1 | | 2/2017 | Spataro |
| 2017/0088754 A1 | | 3/2017 | Sustic et al. |
| 2018/0148616 A1 | | 5/2018 | Okazaki et al. |
| 2019/0256747 A1 | | 8/2019 | Marchini et al. |
| 2019/0382631 A1 * | | 12/2019 | Gu ......................... C09J 123/14 |
| 2020/0010742 A1 † | | 1/2020 | Corzani |

FOREIGN PATENT DOCUMENTS

| | | | |
|---|---|---|---|
| WO | 199739075 A1 † | 10/1997 | |
| WO | 1998492249 A1 † | 11/1998 | |
| WO | 200044412 A1 † | 8/2000 | |

\* cited by examiner
† cited by third party

*Primary Examiner* — Lynda Salvatore
(74) *Attorney, Agent, or Firm* — Kristi Halloran; Kirsten Stone

(57) ABSTRACT

The invention features hot melt adhesive compositions including from 50% by weight to 95% by weight of a non-single site catalyzed amorphous poly alpha-olefin copolymer derived from propylene and at least one monomer selected from the group consisting of butene and hexene and having a viscosity of no greater 10,000 cP at 190° C. and from 5% by weight to 45% by weight of a polybutene-1 polymer.

19 Claims, No Drawings

HOT MELT ADHESIVE COMPOSITIONS INCLUDING NON-SINGLE SHE CATALYZED AMORPHOUS POLY ALPHA-OLEFIN POLYMER, AND ARTICLES INCLUDING THE SAME

This application claims priority to and benefit of U.S. Provisional Patent Application No. 62/767,793 filed on Nov. 15, 2018 and U.S. Provisional Patent Application No. 62/885,568 filed on Aug. 21, 2019.

BACKGROUND

Hot melt adhesives are used in the manufacture of disposable absorbent articles, such as diapers and feminine hygiene articles. Such hot melt adhesives are often referred to as construction adhesives, because they are used in the construction of the absorbent article. In the manufacture of disposable diapers for example, hot melt construction adhesives are used to bond the layers of the diaper together e.g. to bond the polymer film back sheet to a nonwoven web back sheet or a nonwoven web top sheet or to bond together other layers within the article. Hot melt adhesive compositions must exhibit certain properties to be commercially useful as construction adhesives. These properties include good adhesion, good mechanical strength, and good cohesive strength. It is further desirable for the hot melt adhesive composition to have a low odor, superior heat stability.

There is a need for alternative hot melt adhesive compositions that exhibit good adhesion and mechanical strength, while further exhibiting a low odor, superior heat stability and are free of certain compounds that can be found in liquid plasticizers and in particular, can be found in oil.

SUMMARY

In one aspect, the invention features a hot melt adhesive composition including from 50% by weight to 95% by weight of a non-single site catalyzed amorphous poly alpha-olefin copolymer derived from propylene and at least one monomer selected from the group consisting of butene and hexene and having a viscosity of no greater 10,000 cP at 190° C. and from 5% by weight to 45% by weight of a polybutene-1 polymer, wherein the hot melt adhesive composition comprises no greater than 10% by weight of an oil.

In one embodiment, the hot melt adhesive composition includes no greater than 10% by weight of a liquid plasticizer. In another embodiment, the hot melt adhesive composition is free of tackifying agent. In a different embodiment, hot melt adhesive composition includes from 5% by weight to 25% by weight of a tackifying agent.

In one embodiment, the amorphous poly alpha-olefin copolymer and the polybutene-1 copolymer include at least 90%, or even at least 95% by weight of the composition. In a different embodiment, the hot melt adhesive composition comprises no greater than 10% by weight of a wax.

In one embodiment, the non-single site catalyzed amorphous poly alpha-olefin copolymer is derived from butene and propylene. In a different embodiment, the non-single site catalyzed amorphous poly alpha-olefin copolymer has a viscosity of no greater 5,000 cP at 190° C. In another embodiment, the hot melt adhesive composition includes from 60% by weight to 90% by weight of the non-single site catalyzed amorphous poly alpha-olefin copolymer.

In one embodiment, the polybutene-polymer is single-site catalyzed. In another embodiment, the polybutene-1 polymer has a density of greater than 0.89. In a different embodiment, the polybutene-1 polymer is a copolymer of polybutene-1 and ethylene. In still another embodiment, the polybutene-1 polymer has a viscosity of 3000 cP to 50,000 cP at 190° C. In one embodiment, the hot melt adhesive composition includes from 5% by weight to 40% by weight of the polybutene-1 copolymer.

In one embodiment, the hot melt adhesive composition further includes from 1% by weight to 7% by weight of a wax selected from a group consisting of Fischer-Tropsch wax and polyethylene wax or a combination thereof. In another embodiment, the hot melt adhesive composition has an Initial Static Peel of from 10 min to 100 min.

In another embodiment, the invention features a disposable absorbent article including a body fluid impermeable back sheet, a nonwoven top sheet, and the hot melt adhesive composition, wherein the body fluid impermeable back sheet is adhered to the nonwoven top sheet through the hot melt adhesive composition.

In another aspect, the invention features a hot melt adhesive composition including from 50% by weight to 95% by weight of a non-single site catalyzed amorphous poly alpha-olefin copolymer derived from propylene and at least one monomer selected from the group consisting of butene and hexene and having a viscosity of no greater 10,000 cP at 190° C. and from 5% by weight to 25% by weight of a polybutene-1 polymer, wherein the hot melt adhesive composition is free of liquid plasticizer.

The hot melt adhesive compositions of this invention maintain strong adhesion properties in the absence of or with a limited amount of tackifying agent. In compositions with no or limited tackifying agent, it is important to find a different way to introduce cohesion or stiffness into the hot melt adhesive composition. In the compositions of this invention, the polybutene-1 polymer is useful for this function.

The hot melt adhesive compositions of this invention can additionally be free of oil or all liquid plasticizers. This is desirable as plasticizers often contain volatile materials or poly aromatic hydrocarbons (PAHs) that are undesirable to the end user.

Other features and advantages will be apparent from the following description of the preferred embodiments and from the claims.

DETAILED DESCRIPTION

Hot Melt Adhesive Composition

The invention features a hot melt adhesive composition including from 50% by weight to 95% by weight of a non-single site catalyzed amorphous poly alpha-olefin copolymer derived from propylene and at least one monomer selected from the group consisting of butene and hexene and having a viscosity of no greater 10,000 cP at 190° C. and from 5% by weight to 45% by weight of a polybutene-1 polymer.

The non-single site catalyzed amorphous poly alpha-olefin copolymer, and the polybutene-1 polymer can comprise at least 70% by weight, at least 75% by weight, at least 80% by weight, at least 90% by weight, or even at least 95% by weight of the composition.

The hot melt adhesive composition has a Brookfield Viscosity of no greater than 20,000 cP, no greater than 10,000 cP, no greater than 7,500 cP, from 500 cP to 20,000 cP, from 500 cP to 10,000 cP, or even from 250 cP to 7,500 cP at 149° C.

The hot melt adhesive composition has an Initial Dynamic Peel of no less than 90 grams' force (gf)/inch (in), no less than 95 gf/in, no less than 100 gf/in, from 90 gf/in to 300 gf/in, from 100 gf/in to 300 gf/in or even from 120 gf/in to 200 gf/in.

The hot melt adhesive composition has an Initial Static Peel of no less than 5 minutes (min), no less than 10 min, no less than 15 min, no less than 20 min, no less than 30 min, from 10 min to 200 min, from 10 min to 100 min, from 20 min to 100 min, or even from 30 min to 100 min.

Non-Single Site Catalyzed Amorphous Poly Alpha-Olefin

The hot melt adhesive composition includes a non-single site catalyzed amorphous alpha-olefin copolymer. The non-single site catalyzed amorphous alpha-olefin polymer is derived from propylene and at least one monomer selected from the group consisting of butene and hexene.

The non-single site catalyzed amorphous alpha-olefin polymer can have a density of no greater than 0.89 g/cm3, exhibits a glass transition temperature (Tg) of no greater than 0° C., no greater than −5° C., no greater than −10° C., no greater than −15° C., or even no greater than −20° C., and exhibits a melt temperature (Tm) of no greater than 130° C., no greater than 125° C., or even no greater than 120° C. Useful non-single site catalyzed amorphous alpha-olefin polymers also exhibit a ΔH (J/g)—first heat of no greater than 25 Joules/gram (J/g), no greater than 20 J/g, no greater than 15 J/g, no greater than 10 J/g, from 0 J/g to 15 J/g, or even from 0 J/g to 10 J/g and a viscosity of at least 50 cP, at least 100 cP, at least 500 cP, no greater than 20,000 cP, no greater than 10,000 cP, from 50 cP, to 10,000 cP, from 50 cP to 8,000 cP, or even from 50 to 5,000 cP at 190° C.

Useful non-single site catalyzed amorphous alpha-olefin copolymers include, e.g., copolymers, terpolymers, higher order polymers, and combinations thereof, derived from propylene and at least one monomer selected from the group consisting of butene and hexene. The non-single site catalyzed amorphous alpha-olefin copolymers can also include additional alpha-olefin monomers including, e.g., ethylene, pentene, heptene, octene, nonene, decene, dodecene, 4-methyl-1-pentene, 3-methyl-1-pentene, 3,5,5-trimethyl-1-hexene, 5-ethyl-1-nonene, and combinations thereof.

The non-single site catalyzed amorphous alpha-olefin polymer is preferably is free of functional groups but optionally includes functional groups (e.g., maleic anhydride, silane, etc.). The non-single site catalyzed propylene-alpha-olefin also preferably has an acid number of zero.

The non-single site catalyzed amorphous alpha-olefin polymer can be prepared using a variety of catalysts including e.g., a Ziegler Natta catalyst.

Useful non-single site catalyzed amorphous alpha-olefin polymers are commercially available under a variety of trade designations including, e.g., REXTAC 2730, REXTAC 2715, REXTAC 2815, AND REXTAC 2830 butene copolymers all of which are available from Rextac LLC (Odessa, Tex.) and VESTOPLAST EP V2094 available from Evonik Corporation (Parsippany, N.J.).

The hot melt adhesive composition can include at least 40% by weight, at least 45% by weight, at least 50% by weight, at least 60% by weight, no greater than 95% by weight, no greater than 90% by weight, from 40% by weight to 95% by weight, from 50% by weight to 95% by weight, from 60% by weight to 90% by weight, from 65% by weight to 90% by weight, or even from 75% by weight to 90% by weight of the non-single site catalyzed amorphous alpha-olefin polymer.

Polybutene-1 Polymer

The hot melt adhesive composition includes a polybutene-1 polymer. The polybutene-1 polymer can be a homopolymer or a copolymer.

Useful polybutene-1-homopolymers and copolymers of the present invention are primarily linear chain molecules with regular and spatially ordered arrangements of ethyl side groups. These side groups result when butene-1 is polymerized across the 1,2-carbon double bond, and along an ethylene chain back bone. When cooled from the melt, the ethyl side groups initially align in a tetragonal spatial arrangement (form II). With time, the tetragonal crystalline phase form transfers into a stable hexagonal spatial arrangement (form I) resulting in an improvement in properties.

Polybutene-1 polymers can be prepared by single site catalyst (e.g. metallocene catalyst) or non-single site catalyst (e.g. Ziegler-Natta catalyst) and can comprise one or more of a variety of alpha-olefins, see for example the butene-1 copolymers taught in U.S. Pat. No. 3,362,940, WO2018007279A 1 and WO2018007280A1.

Polybutene-1 polymers prepared by single site catalyst can be preferred due to their narrow and more consistent molecular weight distribution.

The polybutene-1 polymer can be a copolymer of butene and ethylene. Butene-1/ethylene copolymers, with ethylene comonomer in the range of 0.5-20 mole percent can be useful in the inventive hot melt adhesive compositions.

The polybutene-1 polymer can have a ΔH (J/g)—first heat of at least 18 J/g, at least 20 J/g, from 15 J/g to 50 J/g, or even from 20 J/g to 40 J/g.

The polybutene-1 polymer can have a ΔH (J/g)—second heat of at least 10 J/g, at least 15 J/g, at least 20 J/g, or even from 15 J/g to 35 J/g.

The polybutene-1 polymer can have a density of greater than 0.87, greater than 0.88, greater than 0.89, from 0.89 to 0.94, or even from 0.895 to 0.94.

The polybutene-1 polymer can have a viscosity of at least 50 cP, at least 100 cP, at least 500 cP, at least 3000 cP, no greater than 75,000 cP, no greater than 50,000 cP, no greater than 20,000 cP, from 500 cP to 75,000 cP, from 500 cP to 50,000 cP, from 500 cP to 20,000 cP, or even from 50 to 15,000 cP at 190° C.

Useful polybutene-1 polymers are commercially available under a variety of trade designations including, e.g., KOATTRO PB M 0600 M, KOATTRO PB M 1200M, KOATTRO PB M8911 M and KOATTRO DP 8911 ME from Lyndellbasell Industries N.V. (Rotterdam, Netherlands).

The hot melt adhesive composition can include at least 5% by weight, at least 10% by weight, at least 15% by weight, no greater than 60% by weight, no greater than 50%, no greater than 40% by weight, from 5% by weight to 60% by weight, from 5% by weight to 50% by weight, from 5% by weight to 45% by weight, from 5% by weight to 40% by weight, from 10% by weight to 40% by weight, from 5% by weight to 35% by weight, or even from 5% by weight to 25% of the polybutene-1 polymer.

Tackifying Agent

The hot melt adhesive composition is free of tackifying agent, or optionally includes a limited amount of tackifying agent.

Useful tackifying agents have Ring and Ball softening point of no greater than 160° C., at least 110° C., at least 115° C., at least 120° C., at least 125° C., from 80° C. to 150° C., from 100° C. to 150° C., from 110° C. to 150° C., or even from 120° C. to 150° C.

The tackifying agent can include aromaticity, in some embodiments from 5% by weight to 15% by weight aromatic groups. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; and combinations thereof. Examples of useful polyterpene resins include polyterpene resins, hydrogenated polyterpene resins, and copolymers and terpolymers of natural terpenes (e.g. styrene-terpene, alpha-methyl styrene-terpene and vinyl toluene-terpene). Examples of useful aliphatic and cycloaliphatic petroleum hydrocarbon resins include aliphatic and cycloaliphatic petroleum hydrocarbon resins having Ring and Ball softening points of from about 10° C. to 140° C. (e.g., branched and unbranched C5 resins, C9 resins, and C10 resins) and hydrogenated derivatives thereof.

Useful tackifying agents are commercially available under a variety of trade designations including, e.g., the ESCOREZ series of trade designations from ExxonMobil Chemical Company (Houston, Tex.) including ESCOREZ 5400, ESCOREZ 5415, ESCOREZ 5600, ESCOREZ 5615, ESCOREZ 5637 and ESCOREZ 5340, the EASTOTAC series of trade designations from Eastman Chemical (Kingsport, Tenn.) including EASTOTAC H-100L, EASTOTAC H130W, and EASTOTAC H-142.

The hot melt adhesive composition can include at least 5% by weight, at least 10% by weight, no greater than 40% by weight, no greater than 30% by weight, no greater than 25% by weight, no greater than 20% by weight, from 0% by weight to 40% by weight, from, 0% by weight to 30% by weight, from 5% by weight to 25% by weight, or even from 10% by weight to 20% by weight of tackifying agent.

Liquid Plasticizer

The hot melt adhesive composition is free of plasticizer or can optionally include a limited amount of plasticizer.

The plasticizer is liquid at room temperature. The term "liquid" as used in reference to the plasticizer means that the plasticizer exhibits a kinematic viscosity of no greater than 5000 Centistokes (CST) at 100° C. as determined according to ASTM D445 and a pour point of no greater than 30° C. as determined according to ASTM D97. Suitable classes of liquid plasticizers include, e.g., oils, and oligomeric and low molecular weight polymeric plasticizers that are liquid at room temperature (hereinafter the oligomeric and low molecular weight polymeric plasticizers are referred to as "synthetic liquid plasticizers"). The polymeric and oligomeric liquid plasticizers preferably have a number average molecular weight (Mn) of from 500 g/mole to 7000 g/mole.

The plasticizer can be selected from the group consisting of polybutene and polyisobuylene. The plasticizer can have a Mn of 1000 g/mol. to 5,000 g/mol (performed by Gel Permeation Chromatography (GPC), as reported by the supplier).

In another embodiment, the hot melt adhesive composition comprises no greater than 15% by weight, no greater than 10% by weight, no greater than 5% by weight, or even is free of plasticizer.

In another embodiment, the hot melt adhesive composition comprises no greater than 15% by weight, no greater than 10% by weight, no greater than 5% by weight, or even is free of oil.

Useful plasticizers include, e.g., polybutene, polyisobutylene, polyolefin copolymers (e.g., propylene-ethylene copolymers), oligomerized alpha olefins, oils (e.g., naphthenic petroleum-based oils, paraffinic oils, mineral oils, animal oils, vegetable oils, synthetic oils, derivatives of oils, liquid isoprene, glycerol esters of fatty acids, and combinations thereof), and combinations thereof.

Useful plasticizers are commercially available under a variety of trade designations including, e.g., the INDOPOL series of trade designations from Ineos Oligomers Europe, Limited (Belgium) including INDOPOL H-300, H-1200, H-1500, H-1900, and H-2100 polybutenes, the DURASYN series of trade designations from Ineos Oligomers Europe including DURASYN 127 poly-1-decene, the TPC series of trade designations from TPC Group (Houston Tex.) including TPC 5230, TPC 1105, TPC1160, TPC1285 and TPC1350 polyisobutylenes, the LICOCENE series of trade designations from including, e.g., LICOCENE PPA 330 TP amorphous propylene-ethylene copolymer, KAYDOL mineral oil from Sonnebom (Tarrytown N.Y.), KRYSTOL 550 mineral oil from Petrochem Carless Limited (Surrey, England), and CALSOL 5550 naphthenic oil from Calumet Specialty Products Partners, LP (Indianapolis, Ind.).

The hot melt adhesive composition can include at least 5% by weight, at least 10% by weight, no greater than 30% by weight, no greater than 20% by weight, from 5% by weight to 30% by weight, or even from 5% by weight to 20% by weight of liquid plasticizer.

Wax

The hot melt adhesive composition optionally includes wax. Suitable waxes include non-functionalized waxes, functionalized waxes, and combinations thereof. Examples of suitable non-functionalized waxes include polyolefin waxes (e.g., polypropylene waxes and polyethylene waxes), Fischer Tropsch waxes, paraffin waxes, microcrystalline waxes, metallocene waxes, and combinations thereof (e.g., a combination of two non-functionalized waxes each having a melting point of at least 115° C.). The hot melt adhesive composition preferably includes no greater than 10% by weight, at least 1% by weight, from 1% by weight to 7% by weight, or even from 1% by weight to 5% by weight wax.

Additional Components

The hot melt adhesive composition optionally includes additional components including, e.g., antioxidants, adhesion promoters, ultraviolet light stabilizers, rheology modifiers, biocides, corrosion inhibitors, dehydrators, colorants (e.g., pigments and dyes), fillers, surfactants, flame retardants, additional polymers (e.g. styrene block copolymers, ethylene based olefin polymers (e.g. single site catalyzed ethylene based olefin polymers, etc.), propylene based olefin polymers (e.g. single site catalyzed propylene based olefin polymers, etc.) and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Suitable antioxidants are commercially available under a variety of trade designations including, e.g., the IRGANOX series of trade designations including, e.g., IRGANOX 1010, IRGANOX 565, and IRGANOX 1076 hindered phenolic antioxidants, and IRGAFOS 168 phosphite antioxidant, all of which are available from BASF Corporation (Florham Park, N.J.), and ETHYL 702 4,4'-methylene bis(2,6-di-tert-butylphenol). When present, the adhesive composition preferably includes from 0.1% by weight to 2% by weight antioxidant.

Disposable Absorbent Article

The hot melt adhesive composition can be incorporated in a variety of substrates within the disposable absorbent article including, e.g., films (e.g., polyolefin (e.g., polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers), elastics and tape backings.

The hot melt adhesive composition is also useful in a variety of applications and constructions including, e.g., disposable absorbent articles including, e.g., disposable diapers, adult incontinence products, sanitary napkins, medical dressings (e.g., wound care products), bandages, surgical pads, pet training pads (e.g. puppy pads) and meat-packing products, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue).

The hot melt adhesive composition is useful on substrates made from a variety of fibers including, e.g., natural cellulose fibers such as wood pulp, cotton, silk and wool; synthetic fibers such as nylon, rayon, polyesters, acrylics, polypropylenes, polyethylene, polyvinyl chloride, polyurethane, and glass; recycled fibers, and various combinations thereof.

Various application techniques can be used to apply the hot melt adhesive composition to a substrate including, e.g., slot coating, spraying including, e.g., spiral spraying and random spraying, screen printing, foaming, engraved roller, extrusion and meltblown application techniques.

Methods of Making a Disposable Absorbent Article

The hot melt adhesive composition can be used for construction applications. In a typical construction application in the manufacture of a disposable absorbent article, a body fluid impenneable backsheet is bonded to a nonwoven substrate. The adhesive may also be used to bond at least one additional layer or material selected from the group consisting of absorbents, tissues, elastomeric materials, superabsorbent polymers, and combinations thereof. For example, the adhesive can further be used for backsheet lamination i.e. where the body fluid impermeable backsheet typically a polyolefin film (e.g. polyethylene, polypropylene, ethylene vinyl acetate, ethylene copolymer, etc.) is bonded to a second nonwoven to improve the feel of the disposable article.

The invention will now be described by way of the following examples. All parts, ratios, percentages and amounts stated in the Examples are by weight unless otherwise specified.

EXAMPLES

Test Procedures

Test procedures used in the examples include the following. All ratios and percentages are by weight unless otherwise indicated. The procedures are conducted at room temperature (i.e., an ambient temperature of from about 20° C. to about 25° C.) unless otherwise specified.

Heat of Fusion and Glass Transition Temperature Test Method

Heat of fusion (ΔH) is determined using differential scanning calorimetry according to ASTM E-793-06 entitled, "Standard Test Method for Enthalpies of Fusion and Crystallization by Differential Scanning Calorimetry," using the following conditions:

Heat from 25° C. to 190° C. @ 10° C./min
equilibration for 5 min
Cool 190° C. to 25° C. @ 10° C./min
equilibration for 72 hours
Cool 25° C. to −60° C. @ 10° C./min
equilibration for 5 min
Heat −60° C. to 190° C. @ 10° C./min (first heat)
equilibration for 5 min
Cool 190° C. to −80° C. @ 10° C./min
equilibration for 5 min
Heat −80° C. to 190° C. @ 10° C./min (second heat)
equilibration for 5 min
Cool 190° C. to 25° C. @ 10° C./min ΔH is obtained from the first and second heating cycle. The results are reported in Joules/gram (J/g).

Glass Transition Temperature (Tg) is reported as the onset of the heating cure baseline shift at 10° C./min in ° C. from the first heating cycle.

Propylene Polymer Molecular Weight Test Method

The Gel Permeation Chromatography molecular weight was obtained using a high temperature, High-Performance Liquid Chromatography (HPLC) system with Butylated hydroxytoluene (BHT)-stabilized 1,2,4-Trichorobenzene (TCB) mobile phase. The molecular weight data was calculated versus polystyrene standards.

The following conditions were used: HPLC System: Agilent PL-GPC 220; Mobile Phase: TCB stabilized with 0.125% BHT; Temperature: 160° C.; Columns: PLgel 10 um mixed-B (3); Flow rate: 1.0 milliliter/minute; Injection Volume: 200 micro liters; Concentration: 4.0 milligrams/milliliter. Standards: Polystyrene.

Viscosity Test Method

The viscosity of the hot melt adhesive composition is determined in accordance with ASTM D-3236 entitled, "Standard Test Method for Apparent Viscosity of Hot Melt Adhesives and Coating Materials," (Oct. 31, 1988) using a Brookfield Thermosel Viscometer Model RVDV 2+ and an appropriate spindle. The results are reported in centipoise ("cP").

Molten Gardner Color Test Method

A sample is tested (in the molten state) to determine Gardner color by comparing the color of the sample against the Gardner Color Standards set forth in ASTM D-1544. The comparison is made using a Gardner Delta Comparator equipped with an Illuminator available from Pacific Scientific (Bethesda, Md.). The result is reported as the number corresponding to the Gardner Color Standard.

Thermal Stability Test Method

A 300 gram sample of hot melt adhesive composition is placed in a glass beaker (uncovered) and conditioned in a temperature controlled, forced air oven at 163° C. for 240 hours. Every 24 hours, the molten sample is removed from the oven and a sample removed.

The sample is then tested according to the Viscosity test method and the Molten Gardner Color test method. The measured viscosity is reported in centipoise (cP).

Peel Test Sample Preparation Method

A patterned slot coating applicator, which is 3 inch (76.2 mm) wide, and a laminator are set to an application temperature of 154° C., a nip pressure of 103.4 kilopascal (15 psi), an application weight of 4 g/m², and minimal rewind and unwind tensions so as not to stretch the film. The hot melt adhesive composition is applied continuously at a coat weight of 4 g/m² on an oriented polypropylene nonwoven web having a thickness of 4 mil (0.1 mm) and a basis weight of 0.45 ounces per square yard (15.3 g/m$^2$) as the nonwoven web is passed through the applicator at a speed of from 173.7 meters per minute (m/min) to 192.0 m/min. An embossed non-breathable, layered polyethylene film having a thickness of 0.9 mil (0.23 mm), traveling at the same speed as the nonwoven web, is then nipped into place against the adhesive composition and the nonwoven web to form a laminate. The laminate is then cut as strips of 1 inch in width, along both machine direction (MD) of the coater (dynamic peel).

Dynamic Peel Test Method

Dynamic Peel is determined according to ASTM D1876-01 entitled, "Test Method for Determining Peel Resistance of Adhesive (T-Peel Test Method)," with the exception that the test is run at 30.5 centimeters per minute (12 inches per minute) over a period of 10 seconds and 6 replicates are run. The samples are run on an IMASS Spec-type test instrument. Unless otherwise specified, the test samples are prepared as described in the Sample Preparation test method.

The samples are peeled along the machine coating direction. The average peel value over 10 seconds of peeling is recorded, and the results are reported in grams. The initial Dynamic Peel value is the value measured 24 hours after the sample is prepared. Six replicates are tested and the average value is reported in units of grams of force per centimeter (gf/cm).

Static Peel Test Method

Laminates are prepared according to the Peel Test Sample Preparation method. Test samples, 1 inch wide (25.4 mm), are cut from the laminates. The test samples are hung in an oven at 38° C. in a peel mode. A 26-g weight is placed on the sample. Samples are peeled in the cross-machine direction and the time to failure is measured. The Initial Static Peel value is the value measured 24 hours after the sample is prepared. Five replicates are tested and the average time to fail is reported in minutes.

EXAMPLES

Hot melt adhesive compositions of the examples were prepared by combining the components in the amounts specified (in % by weight (wt %)) and heating the same to from 175° C. to 190° C. with mixing.

The hot melt adhesive compositions of the examples were then tested according to the test methods and the results are reported in Table 1. The test samples used in the Dynamic Peel and Static Peel test methods were constructed with a UNIPRO 45 oriented polypropylene nonwoven web having a thickness of 4 mil (0.1 mm) and a basis weight of 0.45 ounces per square yard (15.3 g/m2) from Midwest Filtration Company as the nonwoven web, and a XP34730 embossed non-breathable, layered polyethylene film back sheet having a thickness of 0.9 mil (0.23 mm) from Berry Global Inc. as the film.

TABLE 1

| Polymer type | REXTAC 2715 APAO Butene-1/ copolymer | REXTAC 2730 APAO Butene-1/ Copolymer | KOATTRO PB M 0600M Polybutene-1 Copolymer | KOATTRO PB M 8911M Polybutene-1 Copolymer | KOATTRO PBM 1200M Polybutene-1 Copolymer |
|---|---|---|---|---|---|
| Viscosity @ 190° C. (cP) | 1500 | 3000 | 13500 | 46600 | 6900 |
| Density | | | .89 | .895 | .908 |
| ΔH (J/g) -first heat | 4.1 | 2.6 | 24.48 | | |
| ΔH (J/g) -second heat | 0 | 0 | 12.3 | | 30.3 |
| Tg (° C.) | −30.8 | −25.8 | −42.4 | | −41.6 |
| Tg (° C.) ASTM D 3418 | | | | | |

ΔH and Tg obtained used the Heat of Fusion and Glass Transition Temperature Test Method unless otherwise noted.

TABLE 2

| | 1 wt % | 2 wt % |
|---|---|---|
| REXTAC RT 2715 | 82.3 | 92.4 |
| KOATTRO PB M 0600M | 15.1 | 5 |
| EPOLENE C-13 | 1.6 | 1.6 |
| EVERNOX 10 | 0.5 | 0.5 |
| EVERNOX 76 | 0.5 | 0.5 |
| Total | 100 | 100 |
| Viscosity at 160° C. (cP) | 4235 | |
| Viscosity at 163° C. (cP) | | |
| Initial Dynamic Peel (gf/in) | 117.3 | 99.9 |

TABLE 3

|  | C1 wt % | C2 wt % | 3 wt % | 4 wt % | 5 wt % | 6 wt % | 7 wt % | 8 wt % | 9 wt % |
|---|---|---|---|---|---|---|---|---|---|
| REXTAC RT 2115 | 80 | | | | | | | | |
| REXTAC RT 2715 | | 69.5 | 22.5 | 27.5 | 35 | 29 | 80 | | |
| REXTAC RT 2730 | | | 50 | 40 | 27.5 | 60 | | 59.5 | 59.5 |
| PURETOL 35 | | 14.8 | | | | | | | |
| KOATTRO PB M 1200M | 17.5 | | | | | | 17.5 | | 14.9 |
| KOATTRO PB M 0600M | | 14.9 | 25 | 30 | 35 | | | 14.9 | |
| KOATTRO M 8911M | | | | | | 10 | | | |
| ESCOREZ 5637 | | | | | | | | 24.8 | |
| LUHUA HD 1120 | | | | | | | | | 24.8 |
| EPOLENE C-13 | 1.5 | | 1.5 | 1.5 | 1.5 | | 1.5 | | |
| EVERNOX 10 | 0.5 | 0.4 | 0.5 | 1 | 1 | 1 | 0.5 | .8 | .8 |
| EVERNOX 76 | 0.5 | 0.4 | 0.5 | | | | 0.5 | | |
| Total | 100 | 100 | 100 | 100 | 100 | 100 | 100 | 100 | 100 |
| Viscosity at 160° C. (cP) | | | | | | | | | |
| Viscosity at 163° C. (cP) | 8325 | 3575 | 7650 | 8500 | 8350 | 6375 | 7300 | 7075 | 5400 |
| Initial Dynamic Peel (g f/in) | 25 | 85.4 | 125 | 120 | 126 | 160 | 156 | 210 | 267 |
| Initial Static Peel (mins) | <1 | <1 | 18.25 | 12.5 | 11 | 52 | 53 | 12.8 | 27.5 |

C1 includes REXTAC RT 2115 which is a non-single site amorphous polyolefin propylene homopolymer available from Rextac LLC (Odessa, Tex.). C1 does not have good adhesion as witnessed by its poor peel values.

C2 includes 14.8% by weight of PURETOL 35 which is white mineral oil available from Petro-Canada Lubricants LLC (Mississauga, Ontario). The addition of 14.8% by weight of oil lowers the peel values of the composition.

Other embodiments are within the claims. Documents referred to herein are hereby incorporated herein to the extent they do not conflict.

What is claimed is:

1. A hot melt adhesive composition comprising:
   a. from 50% by weight to 95% by weight of a non-single site catalyzed amorphous poly alpha-olefin copolymer derived from propylene and at least one monomer selected from the group consisting of butene and hexene and having a viscosity of no greater 10,000 cP at 190° C.; and
   b. from 5% by weight to 45% by weight of a polybutene-1 polymer, wherein the hot melt adhesive composition comprises no greater than 10% by weight of an oil.

2. The hot melt adhesive composition of claim 1 wherein the hot melt adhesive composition comprises no greater than 10% by weight of a liquid plasticizer.

3. The hot melt adhesive composition of claim 1 wherein the hot melt adhesive composition is free of tackifying agent.

4. The hot melt adhesive composition of claim 1 comprising from 5% by weight to 25% by weight of a tackifying agent.

5. The hot melt adhesive composition of claim 1 wherein components a.) and b.) comprise at least 90% by weight of the composition.

6. The hot melt adhesive composition of claim 1 wherein components a.) and b.) comprise at least 95% by weight of the composition.

7. The hot melt adhesive composition of claim 1 wherein the hot melt adhesive composition comprises no greater than 10% by weight of a wax.

8. The hot melt adhesive composition of claim 1 wherein the non-single site catalyzed amorphous poly alpha-olefin copolymer is derived from butene and propylene.

9. The hot melt adhesive composition of claim 1 wherein the non-single site catalyzed amorphous poly alpha-olefin copolymer has a viscosity of no greater 5,000 cP at 190° C.

10. The hot melt adhesive composition of claim 1 comprising from 60% by weight to 90% by weight of the non-single site catalyzed amorphous poly alpha-olefin copolymer.

11. The hot melt adhesive composition of claim 1 wherein the polybutene-1 polymer is single-site catalyzed.

12. The hot melt adhesive composition of claim 1 wherein the polybutene-1 polymer has a density of greater than 0.89.

13. The hot melt adhesive composition of claim 1 wherein the polybutene-1 polymer is a copolymer of polybutene-1 and ethylene.

14. The hot melt adhesive composition of claim 1 wherein the polybutene-1 polymer has a viscosity of 3000 cP to 50,000 cP at 190° C.

15. The hot melt adhesive composition of claim 1 comprising from 5% by weight to 40% by weight of the polybutene-1 polymer.

16. The hot melt adhesive composition of claim 1 further comprising from 1% by weight to 7% by weight of a wax selected from a group consisting of Fischer-Tropsch wax and polyethylene wax or a combination thereof.

17. The hot melt adhesive composition of claim 1 having an Initial Static Peel of from 10 min to 100 min.

18. A disposable absorbent article comprising:
   a.) a body fluid impermeable back sheet,
   b.) a nonwoven top sheet, and
   c.) the hot melt adhesive composition of claim 1, wherein the body fluid impermeable back sheet is adhered to the nonwoven top sheet through the hot melt adhesive composition.

19. A hot melt adhesive composition comprising:
   a. from 50% by weight to 95% by weight of a non-single site catalyzed amorphous poly alpha-olefin copolymer derived from propylene and at least one monomer selected from the group consisting of butene and hexene and having a viscosity of no greater 10,000 cP at 190° C.; and
   b. from 5% by weight to 25% by weight of a polybutene-1 polymer, wherein the hot melt adhesive composition is free of liquid plasticizer.

* * * * *